(12) United States Patent
Serna et al.

(10) Patent No.: US 11,007,009 B2
(45) Date of Patent: May 18, 2021

(54) SYSTEM FOR DENERVATION

(71) Applicant: Abbott Cardiovascular Systems Inc., Santa Clara, CA (US)

(72) Inventors: Benjamyn Serna, Gilroy, CA (US); Jesus Magana, Redwood City, CA (US); Michael Ngo, San Jose, CA (US); John Stankus, Campbell, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 111 days.

(21) Appl. No.: 16/590,239

(22) Filed: Oct. 1, 2019

(65) Prior Publication Data

US 2020/0030025 A1 Jan. 30, 2020

Related U.S. Application Data

(62) Division of application No. 14/994,868, filed on Jan. 13, 2016, now Pat. No. 10,448,994.

(51) Int. Cl.
*A61B 18/14* (2006.01)
*A61B 18/00* (2006.01)
*A61B 17/00* (2006.01)

(52) U.S. Cl.
CPC ............ *A61B 18/1492* (2013.01); *A61B 2017/00526* (2013.01); *A61B 2017/00867* (2013.01); *A61B 2018/00214* (2013.01); *A61B 2018/00404* (2013.01); *A61B 2018/00434* (2013.01); *A61B 2018/00511* (2013.01); *A61B 2018/00577* (2013.01); *A61B 2018/1435* (2013.01); *Y10T 29/49117* (2015.01)

(58) Field of Classification Search
CPC ...... A61B 18/1492; A61B 2017/00526; A61B 2017/00867; A61B 2018/00214; A61B 2018/00404; A61B 2018/00434; A61B 2018/00511; A61B 2018/00577; A61B 2018/1435; Y10T 29/49117
USPC ................................................ 29/825, 592.1
See application file for complete search history.

(56) References Cited

U.S. PATENT DOCUMENTS

| | | | |
|---|---|---|---|
| 5,279,299 A | 1/1994 | Imran | |
| 6,371,928 B1 * | 4/2002 | Mcfann | A61B 17/221 600/434 |
| 6,542,781 B1 | 4/2003 | Koblish et al. | |
| 6,702,811 B2 | 3/2004 | Stewart et al. | |

(Continued)

*Primary Examiner* — Peter Dungba Vo
*Assistant Examiner* — Azm A Parvez
(74) *Attorney, Agent, or Firm* — Fulwider Patton LLP

(57) ABSTRACT

A method for manufacturing a shaping structure having a generally helical profile and configured to support electrodes for delivering electric energy into a cylindrical lumen of a patient. The method comprises providing a mandrel with a circular cylindrical shape and forming a first hole in the mandrel along the elongate axis, such that opposing ends of a bore of the first hole emerge at the proximal end and at the distal end; forming a second hole in the mandrel to extend from the curved surface to connect with the first hole; wrapping a metal wire around the mandrel; and inserting opposing ends of the metal wire into the second and the third hole respectively, and threading the opposing ends of the metal wire until they emerge from the opposing ends of the bore of the first hole; finally, heating the mandrel and the wire.

7 Claims, 12 Drawing Sheets

(56) References Cited

U.S. PATENT DOCUMENTS

| | | |
|---|---|---|
| 7,850,685 B2 | 12/2010 | Kunis et al. |
| 2002/0165532 A1 | 11/2002 | Hill, III et al. |
| 2011/0306851 A1 | 12/2011 | Wang |
| 2012/0136350 A1* | 5/2012 | Goshgarian ........ A61B 18/1492 606/41 |
| 2012/0143293 A1* | 6/2012 | Mauch .............. A61M 25/0138 607/99 |
| 2013/0304062 A1 | 11/2013 | Chan et al. |
| 2014/0276718 A1* | 9/2014 | Turovskiy ............ A61B 18/082 606/31 |

* cited by examiner

SYSTEM FOR DENERVATION

CROSS-REFERENCES TO RELATED APPLICATIONS

This divisional application claims priority from U.S. application Ser. No. 14/994,868, filed Jan. 13, 2016, incorporated by reference in its entirety.

BACKGROUND

This invention relates to methods and devices for treatment of diseases that include congestive heart failure, chronic renal failure and hypertension. Specifically, the invention relates to improving conditions in patients by modulating or blocking signals to the renal nerve.

Congestive Heart Failure (CHF) is a form of heart disease that is becoming ever more common. The number of patients with CHF is expected to grow in increasing numbers as the so-called "Baby Boomers" reach 50 years of age. CHF is a health condition that occurs when the heart becomes damaged, resulting in a reduced blood flow to the organs of the body. If blood flow decreases sufficiently, kidney function becomes impaired and results in fluid retention, abnormal hormone secretions and increased constriction of blood vessels. These results increase the stress on the heart to do work, and further decrease the capacity of the heart to pump blood through the kidney and vascular circulation system. This reduced capacity further reduces blood flow to the kidney. It is believed that this cycle of reduced kidney perfusion is the principal non-cardiac cause perpetuating a patient's downward spiral into CHF. Moreover, the fluid overload and associated clinical symptoms resulting from these changes are predominant causes for excessive hospital admissions, reduced quality of life and overwhelming costs to the health care system.

While many different diseases may cause initial damage to the heart, once such damage is present, CHF is identifiable under two types: Chronic CHF and Acute CHF. Despite its name, the chronic form is the less acute form of the two but is a longer term, slowly progressive, degenerative disease and may lead to cardiac insufficiency. Chronic CHF is clinically categorized by the patient's mere inability to exercise or perform normal activities of daily living.

By contrast, patients with Acute CHF may experience a more severe deterioration in heart function than those with Chronic CHF. The Acute form results in the inability of the heart to maintain sufficient blood flow and pressure to keep vital organs of the body alive. This condition can occur when extra stress (such as by infection) significantly increases the workload on the heart in a patient with an otherwise stable form of CHF. By contrast to a mere stepwise downward progression that is observable in patients with Chronic CHF, a patient suffering Acute CHF may deteriorate rapidly from even the earliest stages of CHF to severe hemodynamic collapse. Moreover, Acute CHF can occur within hours or days following an Acute Myocardial Infarction (AMI), which is a sudden, irreversible injury to the heart muscle, identified in common parlance as a heart attack.

Against this background, the kidneys are known to play an important regulatory role in maintaining the homeostatic balance of the body. The kidneys eliminate foreign chemicals from the body, regulate inorganic substances, and function as endocrine glands to secrete hormonal substances like renin and erythropoietin. The main functions of the kidney are to maintain the water balance of the body and control metabolic homeostasis by making the urine more or less concentrated, thus either reabsorbing or excreting more fluid. However, when renal disease arises, some otherwise ordinary and regular physiological functions may become detrimental to the patient's health. When this occurs, the process is known as overcompensation. In the case of Chronic Renal Failure (CRF) the event of overcompensation may manifest itself as hypertension that has the effect of damaging the heart and blood vessels, and can eventually result in a stroke or death. Thus, without proper function by the kidneys, a patient may suffer water retention, reduced urine flow, and an accumulation of waste toxins in the blood and body. These conditions resulting from reduced renal function, or renal failure (kidney failure), tend to increase the workload placed upon the heart. In a patient, simultaneous occurrence of both CRF and CHF may cause the heart to further deteriorate as the water build-up and blood toxins accumulate due to the poorly functioning kidneys and may, in turn, cause the heart further harm.

It has been observed, in connection with human kidney transplantation, that there is evidence to suggest that the nervous system plays a major role in kidney function. It was noted for example that after a transplant, when all the renal nerves are severed, the kidney was observed to increase excretion of water and sodium. This phenomenon has also been observed in animals when renal nerves are cut or chemically destroyed. The phenomenon has been termed "denervation diuresis" because the denervation acted on a kidney in a similar way to a diuretic medication. Later, observation of "denervation diuresis" was found to be associated with vasodilatation of the renal arterial system that led to the increase of the blood flow through the kidney. This observation was confirmed by the further observation in animals that reducing blood pressure supplying the kidney could reverse the "denervation diuresis".

It was also observed that after several months passed after kidney transplant surgery in successful cases, the "denervation diuresis" in transplant recipients stopped, and the kidney function returned to normal. Initially, it was believed that "renal diuresis" is merely a passing phenomenon and that the nerves conducting signals from the central nervous system to the kidney are not essential for kidney function. Later discoveries led to the present generally held conclusion that the renal nerves have an ability to regenerate, and that the reversal of the "denervation diuresis" is attributable to the growth of the new nerve fibers supplying kidneys with the necessary stimuli.

In summary then, it is known from clinical experience and also from the existing large body of animal research that stimulation of the renal nerve leads to the vasoconstriction of blood vessels supplying the kidney, decreased renal blood flow, decreased removal of water and sodium from the body and increased renin secretion. It is also known that reduction of the sympathetic renal nerve activity, achieved by renal denervation, can beneficially reverse these processes.

There has therefore already been identified a need in the art for methods and devices that may apply the observed effects set forth above to halt and reverse the symptoms of Congestive Heart Failure. Thus, certain methods and devices have already been developed in the art to reduce renal nerve activity, in order to meet the aforesaid need. For example, the following patents and applications are directed to the stated need: U.S. Pat. No. 8,347,891, and U.S. Application 2012/0143293, which are incorporated herein by reference. In some approaches configured to induce selective damage to the renal nerves (renal denervation), manufacturers have developed and used radio frequency (RF) catheters, which, while being minimally invasive, have problems related to positioning electrodes within a vessel, and maintaining uniform contact between the electrodes and the vessel wall. For example, in certain systems for denervation, treatment assemblies are used which comprise a helical shaping structure for supporting a plurality of electrodes which are deployed to place the electrodes in contact with a vessel wall. Experience of using these systems reveals that problems arise when attempting to force each electrode against the vessel wall with an equal force, or approximately equal force. It is found, for example, that some electrodes experience a greater contact force than others, even where the helical member is configured to have a helical diameter of constant magnitude over its length.

Thus, there is a need in the medical arts to produce a system and method for RF-based renal therapy which is relatively simple, accurate, effective, and produces an enhanced measure of electrode apposition control. The present invention addresses these and other needs

SUMMARY OF THE INVENTION

In some embodiments, the invention includes a method for manufacturing a shaping structure having a generally helical profile and configured to support electrodes for delivering electric energy into a cylindrical lumen of a patient. The method comprises providing a mandrel with a circular cylindrical shape and having a proximal end and a distal end, a curved surface between the proximal end and the distal end, and an elongate axis. A first hole is formed in the mandrel along the elongate axis, such that opposing ends of a bore of the first hole emerge at the proximal end and at the distal end. A second hole is formed in the mandrel to extend from the curved surface to connect with the first hole, the second hole lying in a first radial plane of the mandrel. A third hole is formed in the mandrel to extend from the curved surface to connect with the first hole, the third hole lying in a second radial plane of the mandrel. A metal wire is wrapped around the mandrel in an area of the mandrel between the second hole and the third hole. Opposing ends of the metal wire are inserted into the second and the third hole respectively, and threading the opposing ends of the metal wire until they emerge from the opposing ends of the bore of the first hole. At this stage, the mandrel and the wire are heated. In some embodiments, wrapping a metal wire around the mandrel includes wrapping a wire formed of shape memory metal, which may be in some embodiments, a wire formed of a Nickel Titanium alloy. In some embodiments, forming a first hole along the elongate axis comprises forming a first hole that is discontinuous in extent between proximal end and distal end. In some embodiments, forming a second hole includes forming a second hole that forms an angle of between 70 degrees and 90 degrees with the elongate axis. This feature will impart desirable characteristics to the shaping structure. In some embodiments, forming a third hole includes forming a third hole that forms an angle of between 70 degrees and 90 degrees with the elongate axis. This feature imparts the same desirable characteristics. In some embodiments, the mandrel may be formed of metal, but it may also be formed of a ceramic material. In some embodiments, the first radial plane and the second radial plane are not offset from each other, whereby the wire is wrapped a full circumferential loop around the mandrel. However, in other embodiments, the first radial plane and the second radial plane are offset from each other, whereby the wire is wrapped between 1.0 and 1.5 circumferential loops around the mandrel. In some embodiments, forming a first hole includes forming a first hole by molding a ceramic material while the ceramic material is malleable, while in other embodiments, forming a first hole includes forming a hole by drilling. In some embodiments, heating the mandrel and wire includes heating to a temperature of between 510° F. and 540° F., and in some embodiments, the time for heating is a period of between 4.5 minutes and 5.5 minutes. In some embodiments, the mandrel and wire are quenched in water.

In another embodiment the invention is a shaping structure having a generally helical profile and configured to support electrodes for delivering electric energy into a cylindrical lumen of a patient. The shaping structure comprises a wire formed of metal, and having a geometric shape described according to a three dimensional orthogonal coordinate system having an x-axis, a y-axis, and a z-axis. The wire is formed to include a first element extending along the x-axis such that y=0, z=0 at all points on the first element; a second element extending along the x-axis such that y=0, z=0 at all points on the second element; and a third element, positioned between and operably connected with the first element and the second element, wherein the third element follows a spiral path with an axial length, a pitch, p, and a helical radius, r, about the x axis such that for any point on the third element, y=r*cos t, z=r*sin t, x=p*(t/2π), where t is a parameter having a dimension in radians. The third element is connected to the first element by a first connector that is straight and extends between a proximal end of the first element and a distal end of the third element, wherein the first connector forms an angle of between 70 degrees and 90 degrees with the x-axis. In further embodiments, the third element is connected to the second element by a second connector that is straight and extends between a distal end of the second element and a proximal end of the third element, wherein the second connector forms an angle of between 70 degrees and 90 degrees with the x-axis. In some embodiments, the first element and the second element are each between 10 and 20 mm in length. In some embodiments, the pitch is between 10 mm and 15 mm. In further embodiments, the radius is between 6 mm and 12 mm. In some embodiments, the wire is formed of shape memory metal, and has a diameter of between 1.0 mm and 2.0 mm, and the length is between 10 mm and 20 mm.

These and other advantages will become clearer when read in conjunction with the drawings and the detailed description of preferred embodiments.

BRIEF DESCRIPTION OF THE DRAWINGS

Many aspects of the present disclosure can be better understood with reference to the following drawings. The components in the drawings are not necessarily to scale. Instead, emphasis is placed on illustrating the principles of the present disclosure.

FIG. 6AA is an end view of the shaping mandrel seen in FIG. 6A.

FIG. 6AB is and end view of another embodiment of a shaping mandrel.

DETAILED DESCRIPTION OF THE PREFERRED EMBODIMENTS

Figure 1:
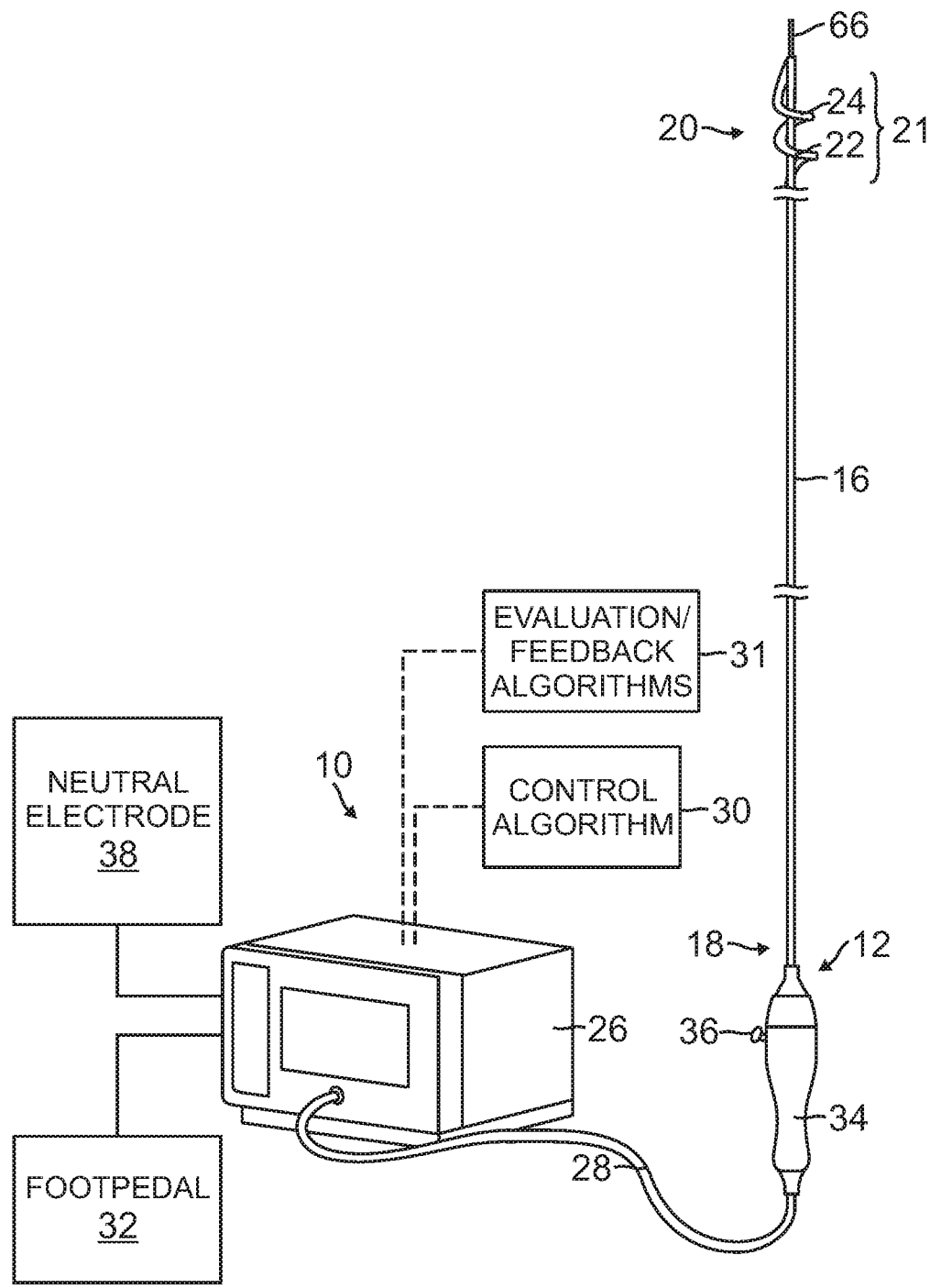
FIG. 1 illustrates an intravascular renal neuromodulation system configured in accordance with an embodiment of the present technology.

The applicants base the present application on the known discovery, as set forth above, that it may be desirable to perform a denervation treatment of the renal artery (renal denervation, or, renal neuromodulation) to positively affect a medical condition. In embodiments of the invention, such treatment may apply energy to zones of the renal artery normal to the artery wall. In some treatments, energy may be applied circumferentially. However, continuous circumferential lesions that extend continuously about a full 360° of the circumference of a cross-section normal to the body lumen or tissue in proximity to the body lumen may increase a risk of acute and/or late stenosis formation within the blood vessel. Therefore, embodiments described herein are directed to forming discrete lesions that do not form a circle in a single plane normal to the axis of the vessel.

Embodiments herein are configured to provide a non-continuous circumferential treatment that is performed over a lengthwise segment of the blood vessel (body lumen), as compared to a continuous circumferential treatment at a single normal cross-section or radial plane. Target structures such as nerves, including nerve fiber bundles, extending along the longitudinal dimension of the vessel are thus circumferentially affected, but not in continuous circumference about a single point of the vessel. Thus, the resulting lesion does not form a continuous circumferential lesion along any normal cross-section or radial plane of the vessel, but rather forms a helical lesion that may in some embodiments be a continuous helical lesion or in other embodiments a helical lesion with discontinuities along its path. This helical characteristic is believed to reduce the risk of acute or late stenosis formation within the blood vessel (body lumen) when compared with lesions that are formed to extend around a normal cross section of the vessel in single plane.

The non-continuous circumferential treatment is achieved in embodiments of the invention via apparatus positioned within a body lumen in proximity to target neural fibers for application of energy to the target neural fibers. The treatment may be induced, for example, via the application of electrical and/or electro-magnetic energy. Such treatment may be achieved, for example, via a thermal or non-thermal electric field, via a continuous or pulsed electric field, or via a stimulation electric field.

In some embodiments, methods and apparatus for real-time monitoring of the treatment and its effects on the target or support structures, and/or in non-target tissue, may be provided. Likewise, real-time monitoring of the energy delivery apparatus may be provided. Power or total energy delivered, impedance and/or the temperature, or other characteristics of the target or non-target tissue, or of the apparatus, additionally or alternatively may be monitored.

When utilizing an electric field to achieve desired circumferentially non-continuous treatment, the electric field parameters may be altered and combined in any combination, as desired. Such parameters can include, but are not limited to, frequency, voltage, power, field strength, pulse width, pulse duration, the shape of the pulse, the number of pulses and/or the interval between pulses (e.g., duty cycle).

When utilizing thermal or indirect thermal mechanisms to achieve the desired treatment, protective elements may be provided to protect the non-target tissue (such as the smooth muscle cells) from thermal damage during the thermally-induced non-continuous circumferential treatment. For example, when heating target nerves or support structures located about a vessel, protective cooling elements, such as convective cooling elements, may be provided to protect the non-target tissue. Likewise, when cooling target nerves or support structures, protective heating elements, such as convective heating elements, may be utilized to protect the non-target tissue. Thermal energy may be applied either directly or indirectly for a brief or a sustained period of time in order to achieve, for example, desired neuromodulation or denervation. Feedback, such as sensed temperature and/or impedance, along target or non-target tissue or along the apparatus, may be used to control and monitor delivery of the thermal energy.

The non-target tissue optionally may be protected during, e.g., the neuromodulation or denervation, by utilizing blood flow as a conductive and/or convective thermal sink that absorbs excess thermal energy (hot or cold). For example, when blood flow is not blocked, the circulating blood may provide a relatively constant temperature medium for removing the excess thermal energy from the non-target tissue during the procedure. The non-target tissue additionally or alternatively may be protected by focusing the thermal (or other) energy on the target or support structures, such that an intensity of the energy is insufficient to induce thermal damage in the non-target tissue distant from the target or support structures.

Embodiments of Catheter Apparatus

FIG. 1 illustrates a renal neuromodulation system 10 configured in accordance with an embodiment of the present technology. The system 10 includes an intravascular intraluminal device 12 operably coupled to an energy source or energy generator 26. In the embodiment shown in FIG. 1, the intraluminal device 12 (e.g., a catheter) includes an elongated shaft 16 having a proximal portion 18, a handle 34 at a proximal region of the proximal portion 18, and a distal portion 20 extending distally relative to the proximal portion 18. (As used herein, the term "operably" connected or coupled means that a connection is formed but permits an indirect connection wherein a further element may be placed between two elements that are operably connected to each other. The intraluminal device 12 further includes a treatment assembly or treatment section 21 at the distal portion 20 of the shaft 16. As explained in further detail below, the treatment assembly 21 can include an array of two or more electrodes 24 configured to be delivered to a renal blood vessel (e.g., a renal artery) in a low-profile configuration. Upon delivery to the target treatment site within the renal blood vessel, the treatment assembly 21 is further configured to be deployed into an expanded state (e.g., a generally helical or spiral configuration) for delivering energy at the treatment site and providing therapeutically-effective electrically- and/or thermally-induced renal neuromodulation. In some embodiments, the treatment assembly 21 may be placed or transformed into the deployed state or arrangement via remote actuation, e.g., via an actuator 36, such as a knob, pin, or lever carried by the handle 34. In other embodiments, however, the treatment assembly 21 may be transformed between the delivery and deployed states using other suitable mechanisms or techniques.

The proximal end of the treatment assembly 21 is carried by or affixed to the distal portion of the elongated shaft 16. A distal end of the treatment assembly 21 may terminate the intraluminal device 12 with, for example, an atraumatic rounded tip or cap. Alternatively, the distal end of the treatment assembly 21 may be configured to engage another element of the system 10 or intraluminal device 12. For example, the distal end of the treatment assembly 21 may define a passageway for engaging a guide wire 66 for delivery of the intraluminal device using over-the-wire ("OTW") or rapid exchange ("RX") techniques.

The energy source or energy generator 26 (e.g., a RF energy generator) is configured to generate a selected form and magnitude of energy for delivery to the target treatment site via the electrodes 24. The energy generator 26 can be electrically coupled to the intraluminal device 12 via a cable 28. At least one supply wire (not shown) passes along the elongated shaft 16 or through a lumen in the elongated shaft 16 to the electrodes 24 and transmits the treatment energy to the electrodes 24. In some embodiments, each electrode 24 includes its own supply wire. In other embodiments, however, two or more electrodes 24 may be electrically coupled to the same supply wire. A control mechanism, such as foot pedal 32, may be connected (e.g., pneumatically connected or electrically connected) to the energy generator 26 to allow the operator to initiate, terminate and, optionally, adjust various operational characteristics of the generator, including, but not limited to, power delivery. The system 10 may also include a remote control device (not shown) that can be positioned in a sterile field and operably coupled to the electrodes 24. The remote control device is configured to allow for selectively turning on/off the electrodes. In other embodiments, the remote control device may be built into the handle assembly 34. The energy generator 26 can be configured to deliver the treatment energy via an automated control algorithm and/or under the control of the clinician. In addition, the energy generator 26 may include one or more evaluation or feedback algorithms to provide feedback to the clinician before, during, and/or after therapy.

Figure 2:
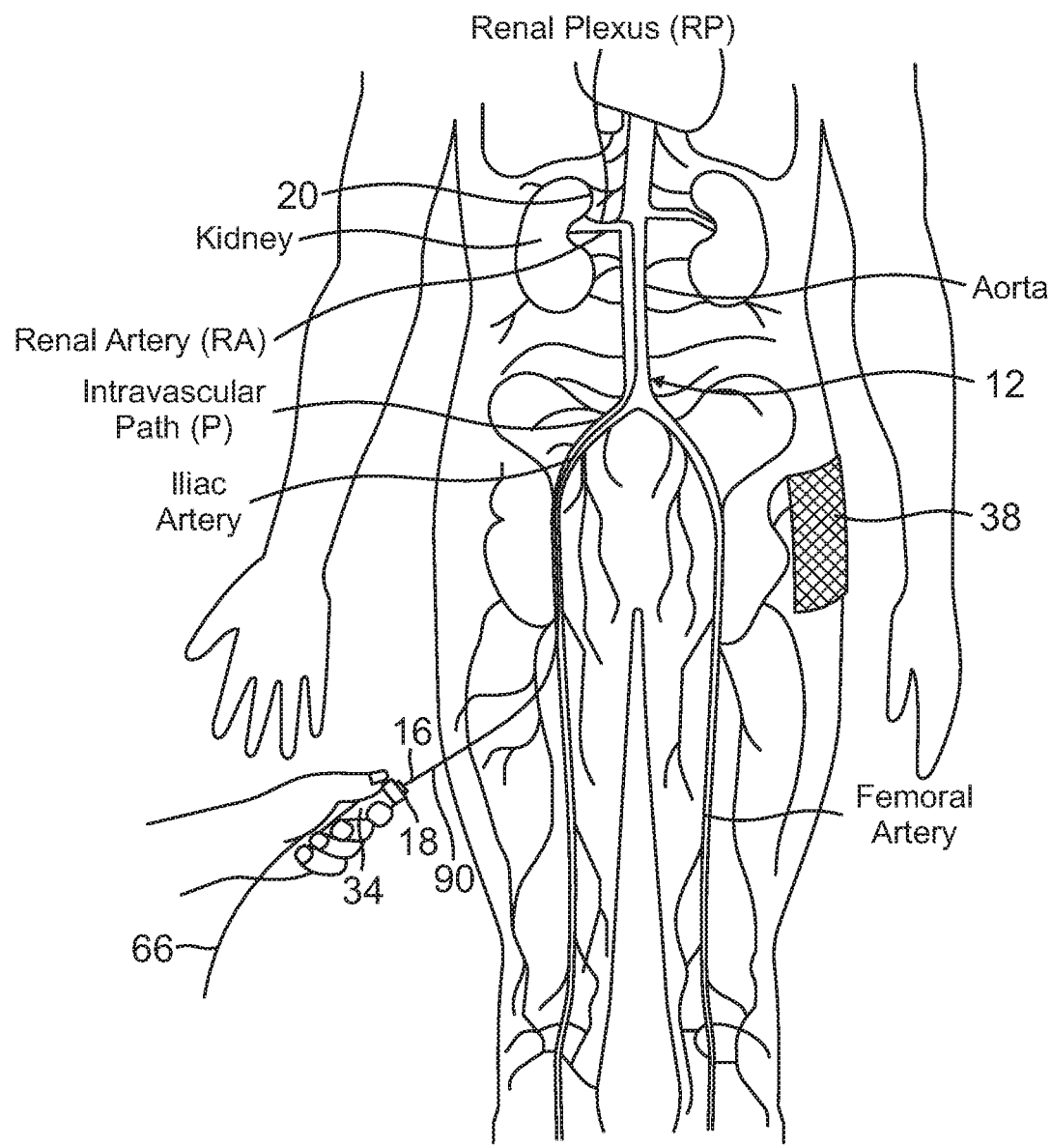
FIG. 2 illustrates modulating renal nerves with a multi-electrode catheter apparatus in accordance with an embodiment of the present technology.

In some embodiments, the system 10 may be configured to provide delivery of a monopolar electric field via the electrodes 24. In such embodiments, a neutral or dispersive electrode may be electrically connected to the energy generator 26 and attached to the exterior of the patient (as shown in FIG. 2). Additionally, one or more sensors (not shown), such as one or more temperature (e.g., thermocouple, thermistor, etc.), impedance, pressure, optical, flow, chemical or other sensors, may be located proximate to or within the electrodes 24 and connected to one or more supply wires (not shown). For example, a total of two supply wires may be included, in which both wires could transmit the signal from the sensor and one wire could serve dual purpose and also convey the energy to the electrodes 24. Alternatively, a different number of supply wires may be used to transmit energy to the electrodes 24.

The energy generator 26 may be part of a device or monitor that may include processing circuitry, such as a microprocessor, and a display. The processing circuitry may be configured to execute stored instructions relating to a control algorithm. The monitor may be configured to communicate with the intraluminal device 12 (e.g., via cable 28) to control power to the electrodes 24 and/or to obtain signals from the electrodes 24 or any associated sensors. The monitor may be configured to provide indications of power levels or sensor data, such as audio, visual or other indications, or may be configured to communicate the information to another device. For example, the energy generator 26 may also be configured to be operably coupled to a catheter lab screen or system for displaying treatment information.

FIG. 2 illustrates modulating renal nerves with an embodiment of the system 10. The intraluminal device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the intraluminal device 12 itself. After the treatment assembly 21 is adequately positioned in the renal artery RA, it can be radially expanded using the handle 34 or other suitable means until the electrodes 24 are in stable contact with the inner wall of the renal artery RA. The purposeful application of energy from the electrodes 24 is then applied to tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP.

The neuromodulating effects are generally a function of, at least in part, power, time, contact between the electrodes 24 and the vessel wall, and blood flow through the vessel. The neuromodulating effects may include denervation, thermal ablation, and non-ablative thermal alteration or damage (e.g., via sustained heating and/or resistive heating).

Figure 3A:
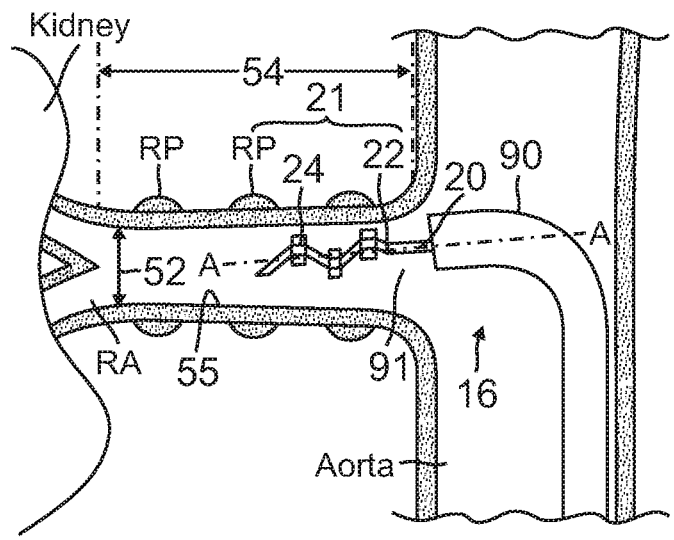
FIG. 3A is a view of a distal portion of a catheter shaft and a multi-electrode array in a delivery state (e.g., low-profile or collapsed configuration) within a renal artery used in conjunction with a guide catheter in accordance with an embodiment of the present technology.
Figure 3B:
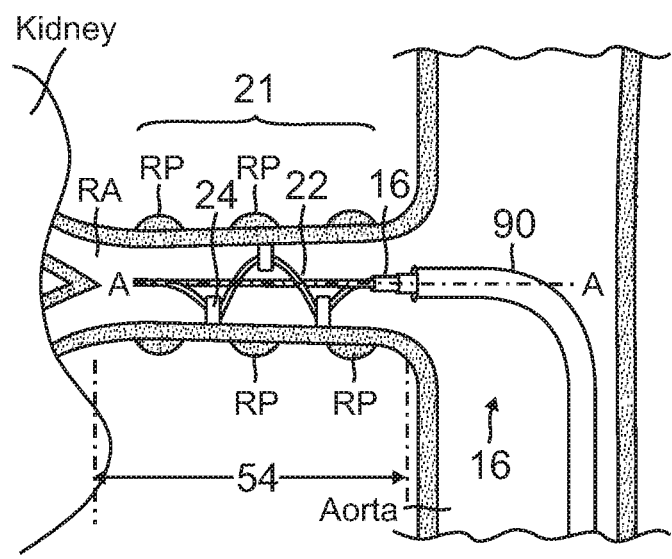
FIG. 3B is a view of the distal portion of the catheter shaft and the multi-electrode array of FIG. 3A in a deployed state (e.g., expanded configuration) within a renal artery in accordance with an embodiment of the technology.

Turning now to a more detailed description of certain embodiments, FIG. 3A is a schematic side view illustrating one embodiment of the distal portion of the shaft 16 and the treatment assembly 21 in a delivery state (e.g., low-profile or collapsed configuration) within a renal artery RA, and FIG. 3B illustrates the treatment assembly 21 in a deployed state (e.g., expanded or helical configuration) within the renal artery. Referring first to FIG. 3A, the collapsed or delivery arrangement of the treatment assembly 21 defines a low profile about the longitudinal axis A-A of the assembly such that a transverse dimension of the treatment assembly 21 is sufficiently small to define a clearance distance between an arterial wall 55 and the intraluminal device 12. The delivery state facilitates insertion and/or removal of the intraluminal device 12 and, if desired, repositioning of the treatment assembly 21 within the renal artery RA.

The distal portion 20 of the shaft 16 may flex in a substantial fashion to gain entrance into a respective left/right renal artery by following a path defined by a guide catheter, a guide wire, or a sheath. For example, the flexing of distal portion 20 may be imparted by the guide catheter 90, such as a renal guide catheter with a preformed bend near the distal end that directs the shaft 16 along a desired path, from the percutaneous insertion site to the renal artery RA. In another embodiment, the intraluminal device 12 may be directed to the treatment site within the renal artery RA by engaging and tracking a guide wire (e.g., guide wire 66 of FIG. 2) that is inserted into the renal artery RA and extends to the percutaneous access site. In operation, the guide wire is preferably first delivered into the renal artery RA and the elongated shaft 16 comprising a guide wire lumen is then passed over the guide wire into the renal artery RA.

After locating the treatment assembly 21 at the distal portion 20 of the shaft 16 in the renal artery RA, the treatment assembly 21 is transformed from its delivery state to its deployed state or deployed arrangement. The transformation may be initiated using an arrangement of device components as described herein with respect to the particular embodiments and their various modes of deployment. As described in greater detail below and in accordance with one or more embodiments of the present technology, the treatment assembly may be deployed by a deployment member, such as for example a pull- or tension-wire engaged with the shaping structure of the treatment assembly to apply a deforming or shaping force to the assembly to transform it into its deployed state.

Further manipulation of the shaping structure 22 and the electrodes 24 within the respective renal artery RA establishes apposition of the electrodes 24 against the tissue along an interior wall of the respective renal artery RA. For example, as shown in FIG. 3B, the treatment assembly 21 is expanded within the renal artery RA such that the electrodes 24 are in contact with the renal artery wall 55.

As best seen in FIG. 3B, in the deployed state, the treatment assembly 21 defines a substantially helical shaping structure 22 in contact with the renal artery wall 55 along a helical path. One advantage of this arrangement is that pressure from the shaping structure can be applied to a large range of radial directions without applying pressure to a circumference of the vessel. Thus, the helically-shaped treatment assembly 21 is configured to provide stable contact between the electrodes 24 and the artery wall 55 when the wall moves in any direction. Furthermore, pressure applied to the vessel wall 55 along a helical path is less likely to stretch or distend a circumference of a vessel that could thereby cause injury to the vessel tissue. Still another feature of the expanded shaping structure is that it may contact the vessel wall in a large range of radial directions and maintain a sufficiently open lumen in the vessel allowing blood to flow through the helix during therapy.

As best seen in FIG. 3B, in the deployed state, the shaping structure 22 defines a maximum axial length of the treatment assembly 21 that is approximately equal to or less than a renal artery length 54 of a main renal artery (i.e., a section of a renal artery proximal to a bifurcation). Because this length can vary from patient to patient, it is envisioned that the deployed helical-shaped shaping structure 22 may be fabricated in different sizes (e.g., with varying lengths and/or diameters) that may be appropriate for different patients. Referring to FIG. 3B, in the deployed state, the helical-shaped treatment assembly 21 provides for circumferentially discontinuous contact between the electrodes 24 and the inner wall 55 of the renal artery RA. That is, the helical path may comprise a partial arc (i.e., <360°), a complete arc (i.e., 360°) or a more than complete arc (i.e., >360°) along the inner wall of a vessel about the longitudinal axis of the vessel.

Figure 4A:
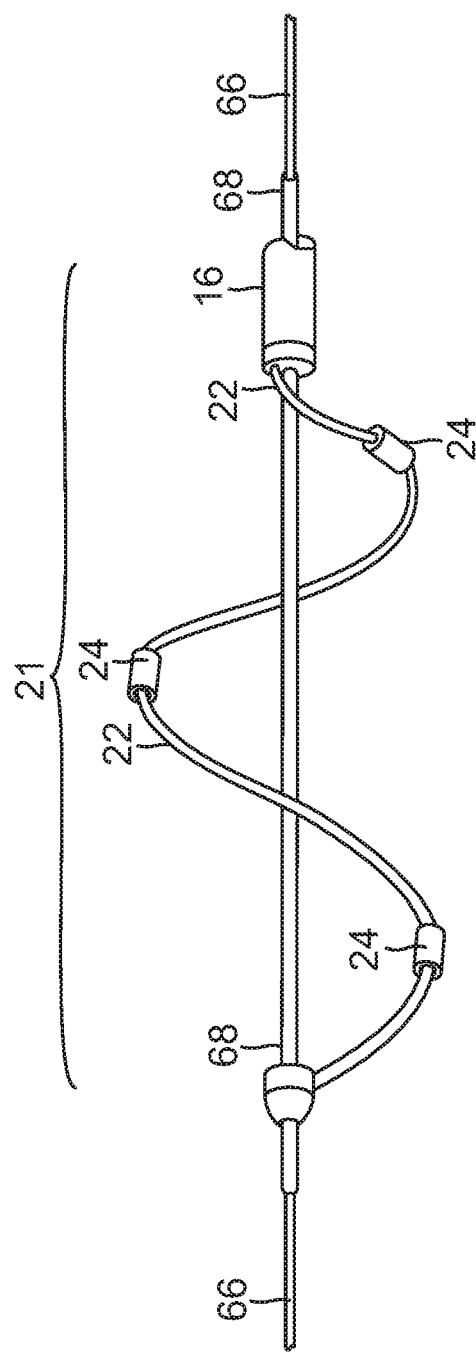
FIG. 4A is a schematic side view of an embodiment of the present technology, shown in an expanded condition for deployment.
Figure 4B:
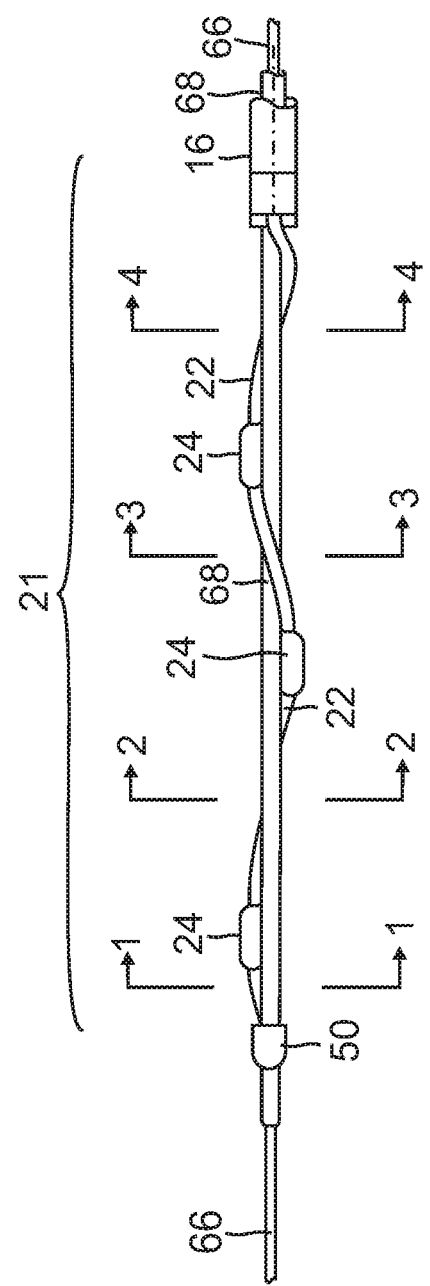
FIG. 4B is a schematic side view of the embodiment of FIG. 4A, shown in a collapsed condition for delivery.

FIGS. 4A and 4B illustrate in more detail a distal portion of an intraluminal device 12 configured in accordance with embodiments of the present technology. More specifically, FIGS. 4A and 4B illustrate a treatment assembly 21 having an elongate shaping structure 22 helically wrapped about a deployment member 68 with a plurality of electrodes 24 disposed about the shaping structure 22.

In the illustrated embodiment, a distal region or portion of the shaping structure 22 terminates in an end piece (e.g., a conical or bullet-shaped tip 50) or, alternatively, a collar, shaft, or cap. The tip 50 can include a rounded distal portion to facilitate atraumatic insertion of the intraluminal device 12 into a renal artery. A proximal region or portion of the shaping structure 22 is coupled to and affixed to the elongated shaft 16 of the intraluminal device 12. The elongated shaft 16 defines a central passageway for passage of a deployment member 68. The deployment member 68 may be, for example, a solid wire made from a metal or polymer. The deployment member 68 extends from the elongated shaft 16 and is affixed to the distal region 22b of the shaping structure 22 at the tip 50. Moreover, the deployment member 68 slidably passes through the elongated shaft 16 to an actuator 36 in a handle assembly 34.

In this embodiment, the deployment member 68 is configured to move distally and proximally through the elongated shaft 16 so as to move the distal region of the shaping structure 22 accordingly. Distal and proximal movement of the distal region respectively lengthen and shorten the axial length of the helix of the shaping structure 22 so as to transform the treatment assembly 21 between a delivery (FIG. 4B) and deployed state (FIG. 4A) such that the electrodes 24 move a radial distance to engage the walls of the renal artery (not shown).

In a preferred embodiment, deployment member 68 comprises a hollow tube defining an internal passage for a guide wire 66 to facilitate insertion of the treatment assembly 21 through an intravascular path to a renal artery. Accordingly, the intraluminal device 12 may be configured for an OTW or RX delivery. The deployment member 68 defines an internal lumen extending through the deployment member and composed of, for example, a polyimide tube with wall thickness less than about 0.003 inch (0.08 mm) (e.g., about 0.001 inch (0.02 mm)) and a lumen with a diameter of less than about 0.015 inch (0.38 mm) (e.g., about 0.014 inch (0.36 mm)). In addition to engaging and tracking along the guide wire 66, the device 12 transforms the configuration of the treatment assembly 21 between the delivery state and the deployed state.

Figure 5A:
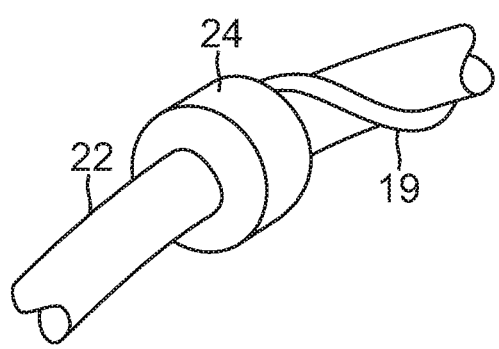
FIG. 5A is a schematic perspective view of an electrode positioned on a shaping structure.
Figure 5B:
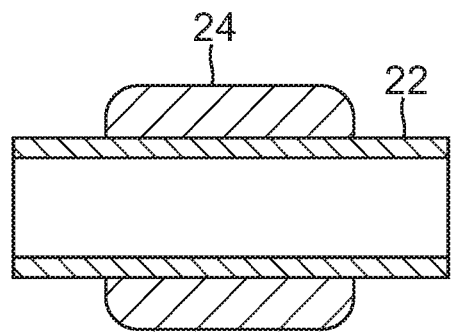
FIG. 5B is a sectional view of the view seen in FIG. 5A.
Figure 5C:
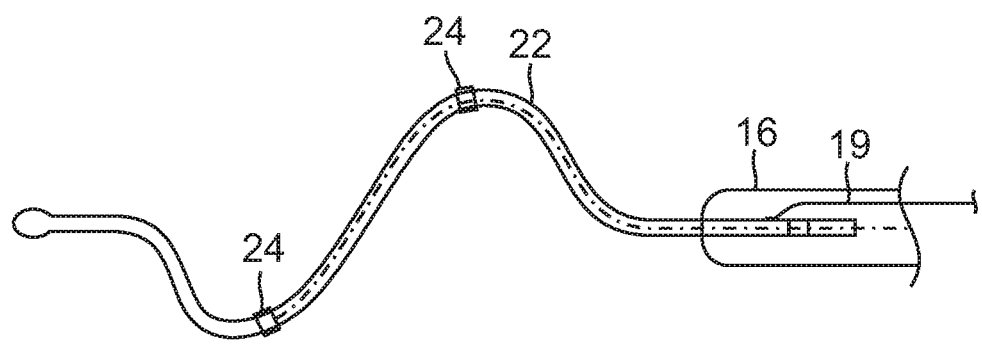
FIG. 5C is a schematic view of an embodiment showing electrical lead line connecting to an electrode.

It should be understood that the embodiments provided herein may be used in conjunction with one or more electrodes 24. As described in greater detail below, the deployed helically-shaped structure carrying the electrodes 24 is configured to provide a therapeutic energy delivery to the renal artery without any repositioning. Illustrative embodiments of the electrodes 24 are shown in FIGS. 5A-5C. The electrodes 24 associated with the shaping structure 22 may be separate elements or may be an integral part of the shaping structure 22. In some patients, it may be desirable to use the electrode(s) 24 to create a single lesion or multiple focal lesions that are spaced around the circumference of the renal artery. A single focal lesion with desired longitudinal and/or circumferential dimensions, one or more full-circle lesions, multiple circumferentially spaced focal lesions at a common longitudinal position, spiral-shaped lesions, interrupted spiral lesions, generally linear lesions, and/or multiple longitudinally spaced discrete focal lesions at a common circumferential position alternatively or additionally may be created. In still further embodiments, the electrodes 24 may be used to create lesions having a variety of other geometric shapes or patterns.

Depending on the size, shape, and number of the electrodes 24, the formed lesions may be spaced apart around the circumference of the renal artery and the same formed lesions also may be spaced apart along the longitudinal axis of the renal artery. In particular embodiments, it is desirable for each formed lesion to cover at least 10% of the vessel circumference to increase the probability of affecting the renal plexus. Furthermore, to achieve denervation of the kidney, it is considered desirable for the formed lesion pattern, as viewed from a proximal or distal end of the vessel, to extend at least approximately all the way around the circumference of the renal artery. In other words, each formed lesion covers an arc of the circumference, and each of the lesions, as viewed from an end of the vessel, abut or overlap adjacent or other lesions in the pattern to create either an actual circumferential lesion or a virtually circumferential lesion. The formed lesions defining an actual circumferential lesion lie in a single plane perpendicular to a longitudinal axis of the renal artery. A virtually circumferential lesion is defined by multiple lesions that may not all lie in a single perpendicular plane, although more than one lesion of the pattern can be so formed. At least one of the formed lesions comprising the virtually circumferential lesion is axially spaced apart from other lesions. In a non-limiting example, a virtually circumferential lesion can comprise six lesions created in a single helical pattern along the renal artery such that each lesion spans an arc extending along at least one sixth of the vessel circumference such that the resulting pattern of lesions completely encompasses the vessel circumference when viewed from an end of the vessel. In other examples, however, a virtually circumferential lesion can comprise a different number of lesions. It is also desirable that each lesion be sufficiently deep to penetrate into and beyond the adventitia to thereby affect the renal plexus. However, lesions that are too deep (e.g., >5 mm) run the risk of interfering with non-target tissue and tissue structures (e.g., a renal vein) so a controlled depth of energy treatment is also desirable.

Referring back to FIG. 3B, the individual electrodes 24 are connected to energy generator 26 (FIG. 1) and are sized and configured to contact an internal wall of the renal artery. In the illustrated embodiment, the electrode 24 may be operated in a monopolar or unipolar mode. In this arrangement, a return path for the applied RF electric field is established, e.g., by an external dispersive electrode (shown as element 38 in FIGS. 1 and 2), also called an indifferent electrode or neutral electrode. The monopolar application of RF electric field energy serves to ohmically or resistively heat tissue in the vicinity of the electrode. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall. Alternatively, a RF electrical field may be delivered with an oscillating or pulsed intensity that does not thermally injure the tissue whereby neuromodulation in the targeted nerves is accomplished by electrical modification of the nerve signals.

The active surface area of the electrode 24 is defined as the energy transmitting area of the element 24 that may be placed in intimate contact against tissue. Too much contact area between the electrode and the vessel wall may create unduly high temperatures at or around the interface between the tissue and the electrode, thereby creating excessive heat generation at this interface. This excessive heat may create a lesion that is circumferentially too large. This may also lead to undesirable thermal application to the vessel wall. In some instances, too much contact can also lead to small, shallow lesions. Too little contact between the electrode and the vessel wall may result in superficial heating of the vessel wall, thereby creating a lesion that is too small (e.g., <10% of vessel circumference) and/or too shallow.

In certain embodiments, the shaping structure 22 may be formed of an electrically conductive material. For example, the shaping structure 22 may be made from nitinol wire, cable, or tube. As shown in FIG. 5C, wire leads 19 may connect the shaping structure 22 to energy generator 26. The shaping structure 22 forms a contact region with the renal artery wall and acts as the electrode 24. In this configuration, the shaping structure 22 is capable of producing a continuous helical lesion. A shaping structure 22 that is configured to be an electrode 24 may optionally comprise sensors positioned on, in, and/or proximate to the shaping structure 22 and may be electrically connected to supply wires.

In other embodiments, the electrically conductive shaping structure 22 is insulated at least in part. That is, the conductive shaping structure is partially covered with an electrically insulating material and the uncovered portions of the shaping structure 22 serve as one or more conductive electrodes 24. The electrodes 24 may be any size, shape, or number, and may be positioned relative to one another as provided herein.

Electrode 24 may be configured to deliver thermal energy, i.e., to heat up and conduct thermal energy to tissue. For example, electrodes may be an electrically resistive element such as a thermistor or a coil made from electrically resistive wire so that when electrical current is passed through the electrode heat is produced. An electrically resistive wire may be for example an alloy such as nickel-chromium with a diameter for example between 48 and 30 AWG. The resistive wire may be electrically insulated for example with polyimide enamel.

Turning now to a novel and advantageous embodiment which is a variation on the kind that is shown in FIGS. 4A and 4B: It has been determined by empirical study that helical shaping structures of this general kind, when expanded in order to make contact between the electrodes 24 and the vascular wall 55 (as in FIG. 3B), may tend to result in a contact pressure at each individual electrode which is unevenly distributed along the length of the shaping structure. For example the distal and proximal electrodes may tend to exert less pressure on the vascular wall than the center electrode(s). This outcome is undesirable because it is well established that electrodes that are in contact with a vessel wall with a greater pressure tend to deliver a greater amount of energy to the vascular tissue and target nerves. It is therefore desirable to have a helical shaping structure in which the distinct pressures between the various electrodes and the vessel wall are evenly distributed along the length of the shaping structure so that the energy delivered may also be evenly distributed. In order to achieve this objective, a novel system and method has been invented for a helical shaping structure carrying a plurality of electrodes.

Figure 6A:
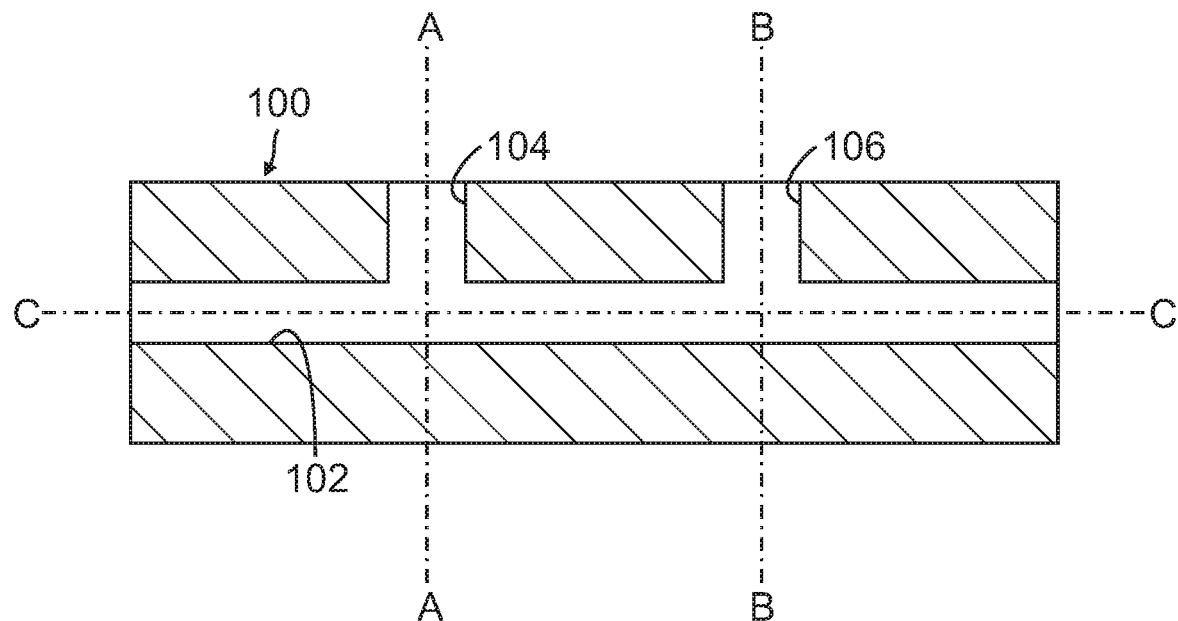
FIG. 6A is a sectional view of a shaping mandrel having features of the invention.
Figure 6B:
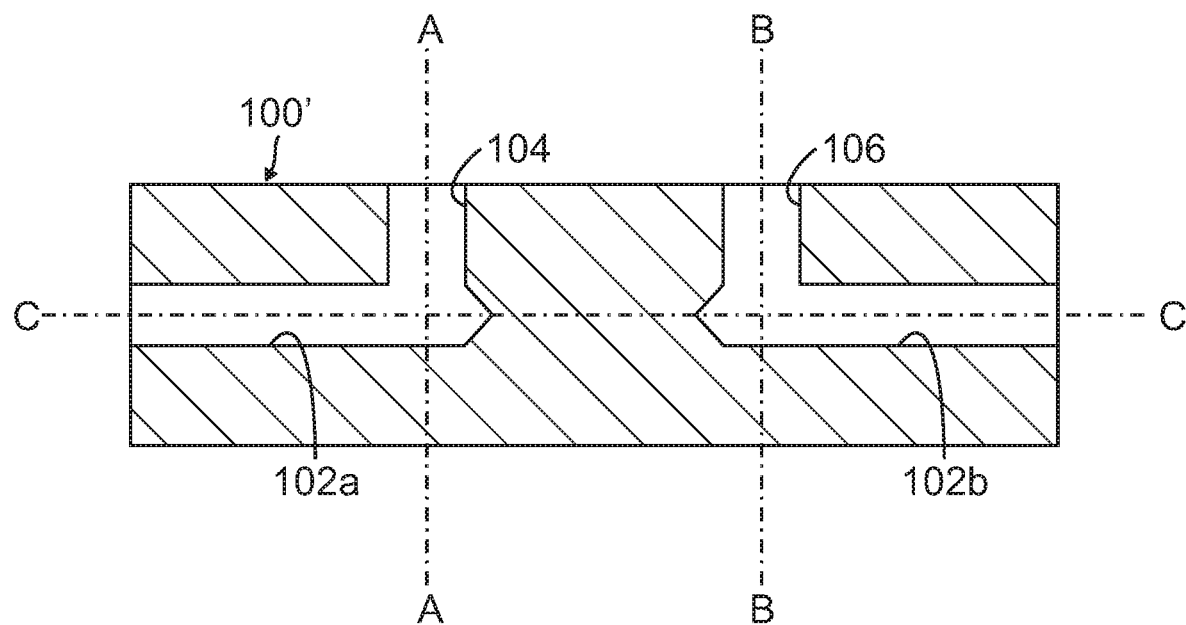
FIG. 6B is a sectional view of another embodiment of a shaping mandrel having features of the invention.
Figure 6C:
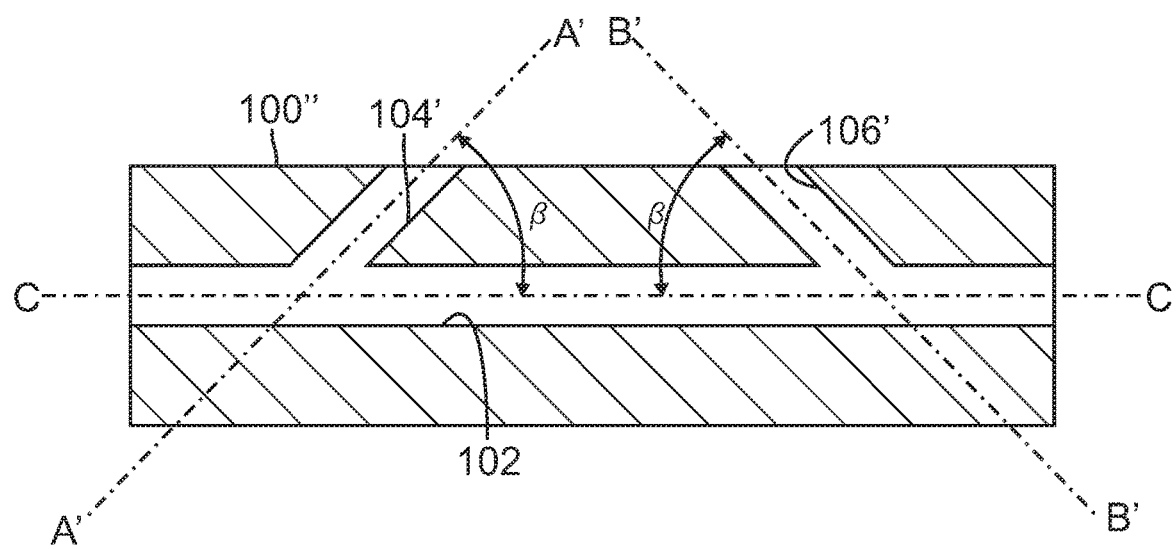
FIG. 6C is a sectional view of yet a further embodiment of a shaping mandrel having features of the invention.
Figure 6A:
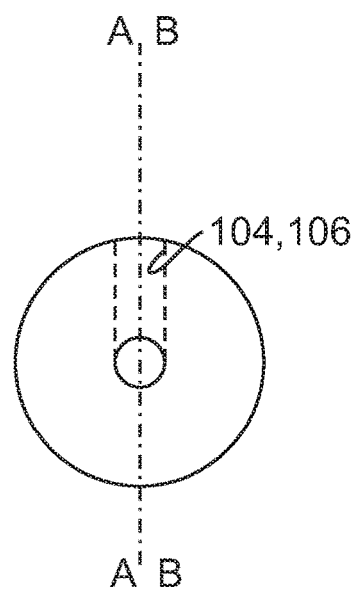
Figure 6A:
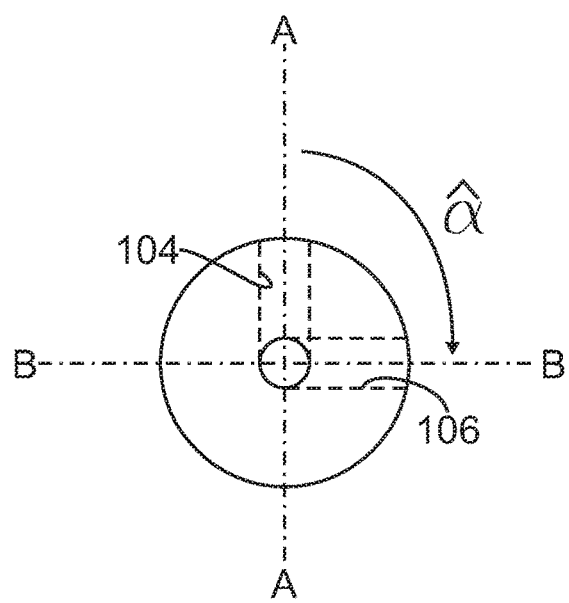

In one embodiment, the invention is a method of manufacturing a helical shaping structure for carrying electrodes in an RF ablation system and which addresses problems in the art. Initially, a cylindrical template mandrel is prepared. As seen in FIGS. 6A-C through FIG. 8, in some embodiments, a short metallic cylinder 100 may be cut from a longer metal rod, leaving a cylinder about 8 mm in diameter and about 90 mm in length. In an embodiment exemplified in FIG. 6A, a hole 102 may be drilled down the axis C-C of the cylinder to provide a continuous bore from one end to the other. Then, two radially oriented holes 104, 106 may be formed for example by drilling into the cylinder from its external curved surface along axes A-A and B-B to meet up with axial hole 102, perpendicularly in some embodiments. In another embodiment exemplified in FIG. 6B, a central hole may be formed in two stages, by drilling an axial first hole 102a in from one end but not completely to the center of the cylinder. Then, a second axial hole 102b may be drilled in from the opposite end, also not to the center of the cylinder. Thereafter, two radial holes 104, 106 may be drilled from the surface of the cylinder to meet up with the axial hole(s). In yet another embodiment exemplified in FIG. 6C, radial holes 104', 106' may be drilled along axes A'-A' and B'-B' respectively which lie in a radial plane of the cylindrical mandrel, but which are each drilled in at an angle β to the central axis C-C. The angle β (beta) may range from 70 degrees, and at the limit, represented by the embodiment in FIGS. 6A and 6B, may be 90 degrees. Once the mandrel is complete, the lip of each radial hole at its point of entry into the cylinder may be angled to provide a gently angled entry point for a wire element that will eventually be inserted therein. In other embodiments, the radial holes 104, 106 or 104', 106' may be offset from each other in a circular plane about the central axis C-C so that they do not lie in the same radial plane. This effect is exemplified by comparing FIG. 6AA with FIG. 6AB. FIG. 6AA is an end view of a mandrel such as the mandrel in FIG. 6A and FIG. 8, in which the radial holes along axes A-A and B-B respectively lie on a single radial plane. FIG. 6AB shows that the axis B-B of second radial hole 106 has been rotated by an angle α (alpha) about the central axis, and no longer shares the same radial plane as hole 104. In the embodiment exemplified in FIG. 6AB, the angle α is ninety degrees, or π/2 radians.

Figure 7:
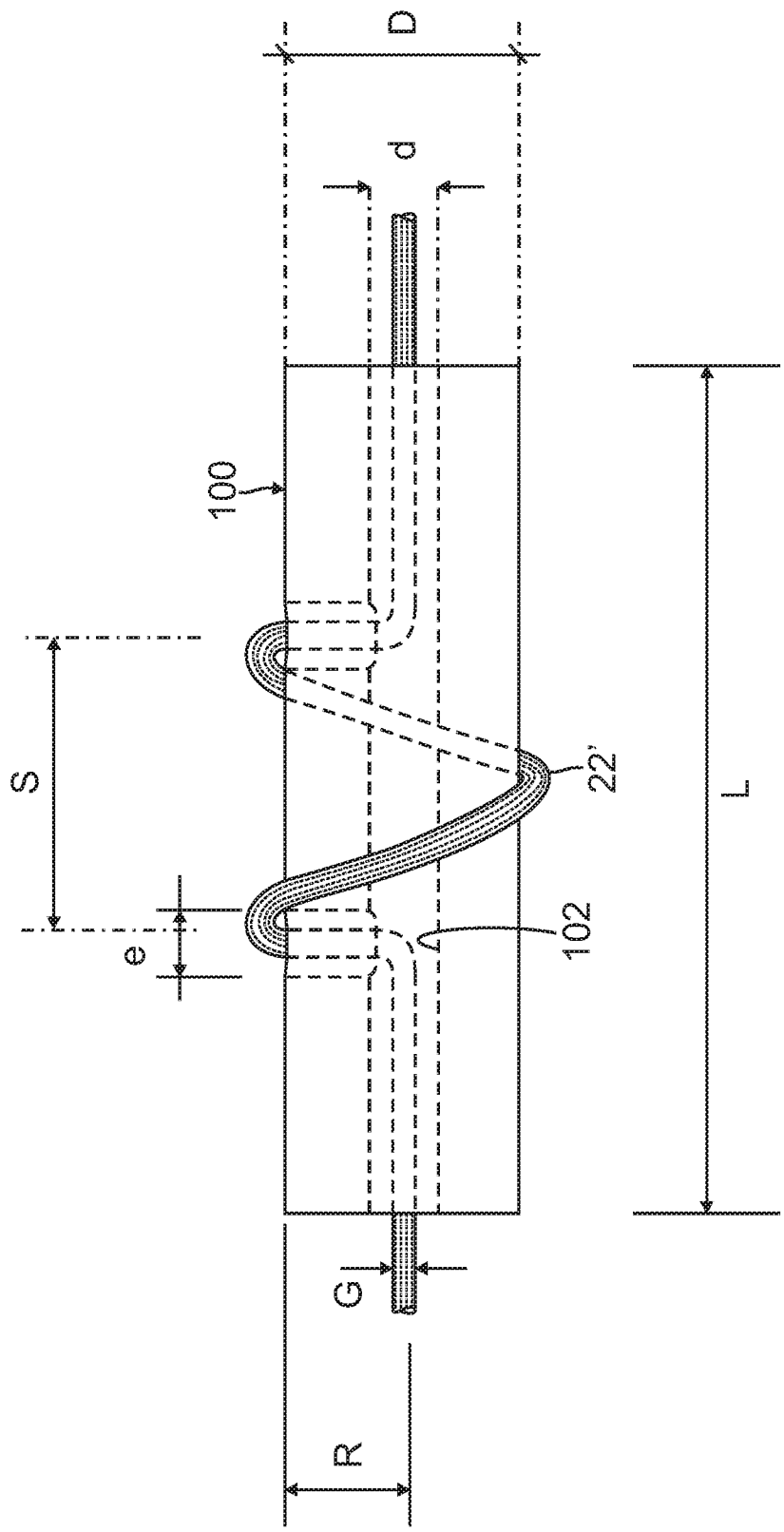
FIG. 7 is a side elevational view of a shaping mandrel in conjunction with a shaping structure, according to one embodiment.
Figure 8:
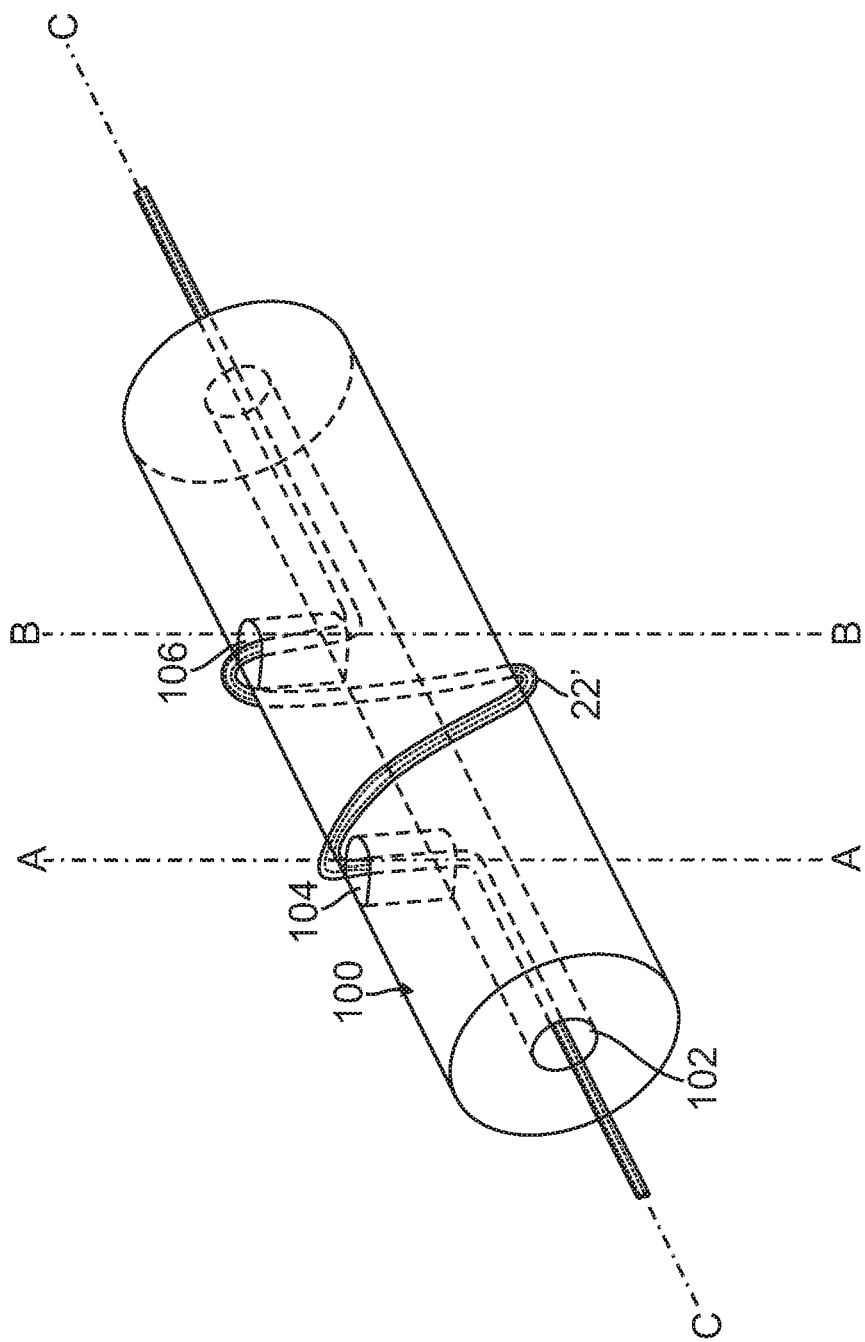
FIG. 8 is a perspective view of the shaping mandrel seen in FIG. 7.

In one example, and with reference to FIG. 7, the dimensions of one embodiment of a shaping mandrel 100 may be as follows: Outer Diameter, D, 8 mm; Inner Diameter, d, 2 mm; wall thickness, R, 3 mm; radial hole spacing, S, 11 mm; length, L, 90 mm; radial holes, d, 2 mm.

In another embodiment, the cylinder 100 may be formed from a ceramic material suitable for withstanding temperatures up to 600° F. The holes may be formed by drilling holes in the ceramic material before the material is completely set hard, after which it is set hard by heating or other known process. Alternatively, cylindrical shafts may be inserted into the ceramic material while it is still in a malleable condition to impart the desired shape to the finished product. When the ceramic material is set sufficiently hard, the shafts may be removed, and the ceramic may be hardened by heating.

Once the holes are thus formed in the cylinder, a length of metal wire may be chosen to form a shaping structure 22' that will be applied to the tip of the catheter 16. In one embodiment, the metal wire may comprise a shape memory alloy such as a Nickel Titanium alloy, and will have the form of an elongate length of cylindrical wire. The length of metal wire is then threaded into the holes 104, 106, 102 formed in the cylinder, as exemplified in FIG. 7 and FIG. 8. This may be easily accomplished by threading one end of the wire down first radial hole 104, and the opposite end of the wire down second radial hole 106. Small bends may be pre-applied to the ends of the wire so that the wire can be threadingly turned around the corner at the end of the radial holes, and thence to emerge from opposite ends of the axial hole 102, as may be seen in FIGS. 7 and 8. It will be appreciated that in an embodiment in which the axial hole 102 does not extend all the way through the cylinder (such as exemplified in FIG. 6B), but terminates at the point of intersection with the radial holes 102, 104, threading the wire through the cylinder may actually be slightly easier because the wire does not have the "option" of turning towards the center of the cylinder when inserted down a radial hole. Once the wire is thus threaded through the mandrel, the ends are pulled taut and clamped against the mandrel (clamps not shown in the figures).

In a further embodiment, both the metal and the ceramic embodiments of the cylinder, once formed, may be split in half along the axis of the cylinder. This feature will facilitate introduction of the wire into, and ultimate removal from, the holes while the two halves of the cylinder are separated. When the wire is satisfactorily placed in the holes, the two halves of the cylinder may be put back together again, and held together by wire or a clamping device during the following annealing process.

In one embodiment, an annealing process may be applied to the metal wire, and this process may include the following steps. A heating oven is set to between 510° F. and 540° F. The wire and shaping mandrel assembly are then laid flat inside the oven for 5 minutes. Thereafter, the wire and mandrel are promptly removed and quenched in room temperature water for 30 seconds. The metal wire is then removed from the shaping mandrel. It will be appreciated that the holes that are drilled in the mandrel may have a diameter that exceeds the diameter of the wire. This oversizing will permit the wire to be easily withdrawn from the mandrel without distorting the wire.

Figure 12:
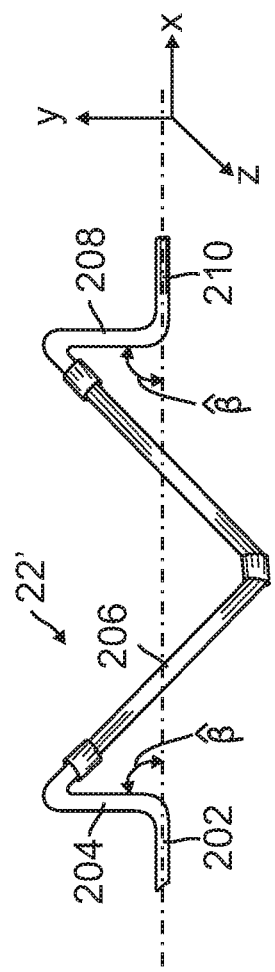
FIG. 12 is a side elevational view of one embodiment of a component of the invention, shown in conjunction with a coordinate axis system.
Figure 13:
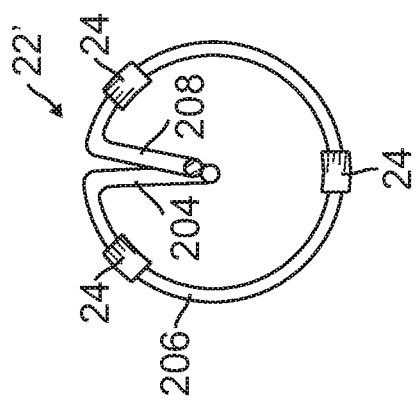
FIG. 13 is an end view of the component shown in FIG. 12, shown in conjunction with the coordinate system.

The resulting shaping structure 22' may have, in one embodiment, the following geometric features, which are described here using a three dimensional coordinate system having x, y, and z orthogonal axes, and with reference to FIG. 12 and FIG. 13. As used herein, the "pitch" of the helical shaping structure is the length over which it traverses 2π radians (a full circle), or over which it would traverse 2π radians if extended far enough. As shown in FIG. 7, the pitch of that embodiment corresponds with the hole spacing, S, of the mandrel. However, in other embodiments described herein, the pitch may not coincide with the hole spacing of the mandrel.

With respect to FIGS. 12 and 13, it is shown that the shaping structure may include:

A first element (a distal leg) 202 extending along the x-axis such that y=0, z=0 for all points along the first element, and x may extend for between 10 mm and 20 mm in length;

A second element (a proximal leg) 210 extending along the x-axis such that y=0, z=0 for all points along the second element, and x may extend for between 10 mm and 20 mm in length. In geometric terms, for the first and second elements, r=0 (r is defined below); and A third element (a helical portion) 206, positioned between and operably connected with the first element and the second element, wherein the third element follows a spiral shape centered about the x axis having a spiral radius r. Here, y=r*cos t, z=r*cost t, x=pitch*(t/2π), wherein r is a radius of the helix, and t is a parameter having the dimension of radians. The actual length of the third element along the x axis is, in embodiments, between 10 mm and 20 mm.

A first connector 204 that is straight is provided to extend between a proximal end of the first element 202 and a distal end of the third element 206, wherein the first connector 204 forms an angle β (beta) of between 70 degrees and 90 degrees with the x-axis as shown in FIG. 12. It will be understood that the angle β here will be the same angle β as that given to the holes 140 and 106 in the mandrel 100'' and seen in FIG. 6C and will acquire that magnitude during the annealing process.

A second connector 208 that is straight is provided to extend between a distal end of the second element 210 and a proximal end of the third element 206, wherein the second connector 208 forms an angle β (beta) of between 70 degrees and 90 degrees with the x-axis. It will be understood that the angle β will be the same angle β as that given to the mandrel 100'' and seen in FIG. 6C and will acquire that magnitude during the annealing process.

Figure 9:
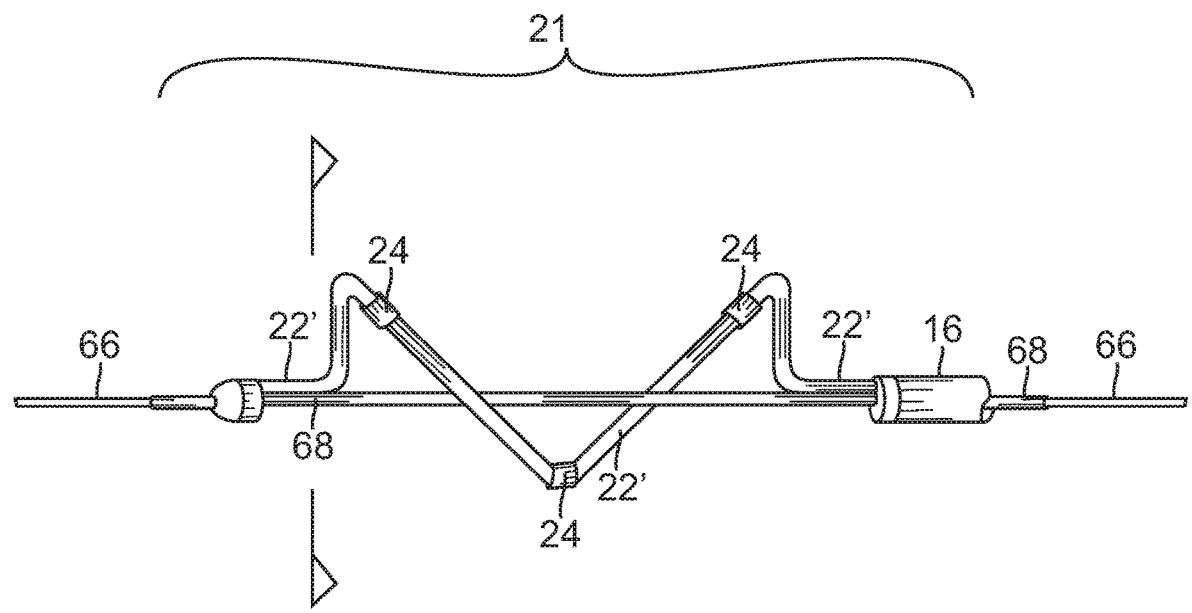
FIG. 9 is a side elevational view of a further embodiment of a treatment assembly having features of the invention, shown in a first expanded condition.
Figure 10:
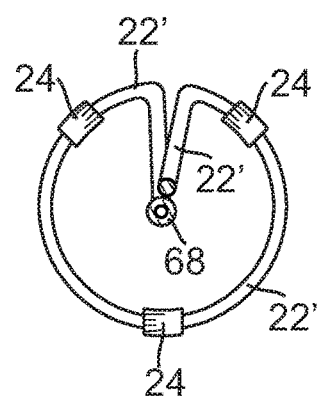
FIG. 10 is an end view of the treatment assembly exemplified in FIG. 9.
Figure 11:
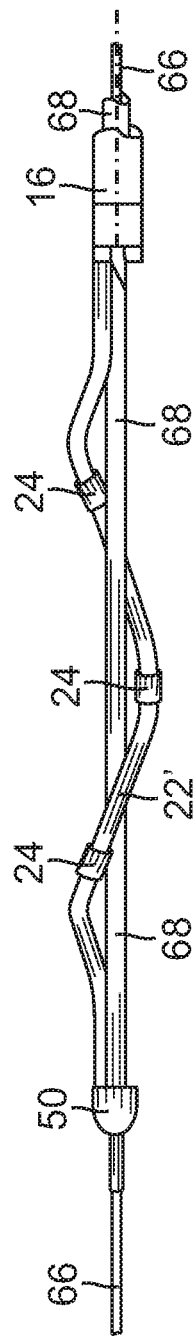
FIG. 11 is a side elevational view of the treatment assembly of FIG. 9, shown in a second collapsed condition.

Once a shaping structure is formed according to one of the above described embodiments, it may be connected to the distal tip of a delivery catheter, as seen in FIG. 9 and FIG. 10. In these figures, all the features of a treatment assembly 21 such as previously described are provided, except that in the present embodiment the shaping structure 22' replaces the shaping structure 22 previously described and seen in FIGS. 4A and 4B. It will be understood with reference to FIGS. 9 and 10 that the shaping structure 22' presents a helical shape that is geometrically different than a shape that results by merely stretching a shaping structure in the form of a straight wire along the tip of a catheter, and wrapping it around the deployment member 68 a desired number of revolutions (as may be envisaged with reference to FIG. 4B), before deploying the shaping structure by pulling the deployment member. It has been determined that the resulting novel shape of the shaping structure 22' as described by the present application is significantly different, and provides a more even distribution of ablation energy from the electrodes in use than that of the embodiment described in relation to FIGS. 4a and 4B.

As previously discussed, energy delivery may be monitored and controlled via data collected with one or more sensors, such as temperature sensors (e.g., thermocouples, thermistors, etc.), impedance sensors, pressure sensors, optical sensors, flow sensors, chemical sensors, etc., which may be incorporated into or on the electrodes 24, the shaping structure 22', and/or in/on adjacent areas on the distal portion 20. A sensor may be incorporated into the electrode(s) 24 in a manner that specifies whether the sensor(s) are in contact with tissue at the treatment site and/or are facing blood flow. The ability to specify sensor placement relative to tissue and blood flow is highly significant, since a temperature gradient across the electrode from the side facing blood flow to the side in contact with the vessel wall may be up to about 15° C. Significant gradients across the electrode in other sensed data (e.g., flow, pressure, impedance, etc.) also are expected.

The sensor(s) may, for example, be incorporated on the side of one or more electrodes 24 that contact the vessel wall at the treatment site during power and energy delivery or may be incorporated on the opposing side of one or more electrodes 24 that face blood flow during energy delivery, and/or may be incorporated within certain regions of the electrodes 24 (e.g., distal, proximal, quadrants, etc.). In some embodiments, multiple sensors may be provided at multiple positions along the electrode or electrode array and/or relative to blood flow. For example, a plurality of circumferentially and/or longitudinally spaced sensors may be provided. In one embodiment, a first sensor may contact the vessel wall during treatment, and a second sensor may face blood flow.

Additionally or alternatively, various microsensors may be used to acquire data corresponding to the electrodes 24, the vessel wall and/or the blood flowing across the electrodes 24. For example, arrays of micro thermocouples and/or impedance sensors may be implemented to acquire data along the electrodes 24 or other parts of the intraluminal device. Sensor data may be acquired or monitored prior to, simultaneous with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

Although preferred illustrative variations of the present invention are described above, it will be apparent to those skilled in the art that various changes and modifications may be made thereto without departing from the invention. For example, it will be appreciated that combinations of the features of different embodiments may be combined to form another embodiment. Furthermore, although in the described embodiments the apparatus and methods are for conducting in a blood vessel, it should be understood that treatment alternatively may be conducted in other body lumens. It is intended in the appended claims to cover all such changes and modifications that fall within the true spirit and scope of the invention.

We claim:

1. A treatment assembly, attached to a distal end of a catheter, and configured to support electrodes for delivering electric energy into a cylindrical lumen of a patient, the treatment assembly comprising:

a wire having a first end and a second end opposite the first end, formed of metal, and having a geometric shape described according to a three dimensional orthogonal coordinate system having an x-axis, a y-axis, and a z-axis, the wire being formed to include:

a first element, having a proximal end and a distal end, extending along the x-axis such that y=0, z=0 at all points on the first element and wherein the distal end of the first element forms the second end of the wire;

a second element, having a proximal end and a distal end, extending along the x-axis such that y=0, z=0 at all points on the second element and wherein the proximal end of the second element forms the first end of the wire; and a third element, having a proximal end and a distal end, positioned between and operably connected with the first element and the second element, wherein the third element follows a spiral path with an axial length, a pitch, p, and a helical radius, r, about the x axis such that for any point on the third element, $y=r*\cos t$, $z=r*\sin t$, $x=p*(t/2\pi)$, where t is a parameter having a dimension in radians;

wherein the third element is connected to the first element by a first connector that is straight and extends between and is connected to the proximal end of the first element and the distal end of the third element, wherein the first connector forms an angle of between 70 degrees and 90 degrees with the x-axis; and further wherein the first end of the wire is attached to an elongate shaft that defines a passageway, and the second end of the wire is attached to an elongate element that slidably passes through the passageway.

2. The treatment assembly of claim 1, wherein the third element is connected to the second element by a second connector that is straight and extends between and is connected to the distal end of the second element and the proximal end of the third element, wherein the second connector forms an angle of between 70 degrees and 90 degrees with the x-axis.

3. The treatment assembly of claim 1, wherein the first element and the second element are each between 10 and 20 mm in length.

4. The treatment assembly of claim 1, wherein the pitch is between 10 mm and 15 mm.

5. The treatment assembly of claim 1, wherein the radius is between 6 mm and 12 mm.

6. The treatment assembly of claim 1, wherein the wire is formed of shape memory metal, and has a diameter of between 1.0 mm and 2.0 mm.

7. The treatment assembly of claim 1, where the length is between 10 mm and 20 mm.

* * * * *